(12) United States Patent
Joseph

(10) Patent No.: US 8,920,728 B2
(45) Date of Patent: Dec. 30, 2014

(54) BIOSENSOR TEST MEMBER AND METHOD FOR MAKING THE SAME

(71) Applicant: Roche Diagnostics Operations, Inc., Indianapolis, IN (US)

(72) Inventor: Abner David Joseph, Carmel, IN (US)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 13/899,892

(22) Filed: May 22, 2013

(65) Prior Publication Data

US 2013/0251591 A1    Sep. 26, 2013

Related U.S. Application Data

(62) Division of application No. 12/862,262, filed on Aug. 24, 2010, now Pat. No. 8,468,680.

(51) Int. Cl.
```
G01N 15/06      (2006.01)
G01N 33/00      (2006.01)
G01N 33/48      (2006.01)
B05D 5/12       (2006.01)
C23C 18/31      (2006.01)
G01N 27/327     (2006.01)
G01N 27/26      (2006.01)
B05D 3/06       (2006.01)
```

(52) U.S. Cl.
CPC . *B05D 5/12* (2013.01); *C23C 18/31* (2013.01); *G01N 27/3272* (2013.01); *G01N 27/26* (2013.01); *B05D 3/06* (2013.01)
USPC ....... 422/82.01; 422/50; 422/68.1; 422/82.02

(58) Field of Classification Search
CPC ........ G01N 15/06; G01N 33/00; G01N 33/48
USPC .............................. 422/50, 68.1, 82.01, 82.02
See application file for complete search history.

(56) References Cited

U.S. PATENT DOCUMENTS

| | | | |
|---|---|---|---|
| 6,737,287 B1 | 5/2004 | Furuse et al. | |
| 6,774,021 B2 | 8/2004 | Fukunaga et al. | |
| 6,805,780 B1 | 10/2004 | Ryu et al. | |

(Continued)

FOREIGN PATENT DOCUMENTS

| WO | WO 97/18464 A1 | 5/1997 |
|---|---|---|
| WO | WO 99/05528 A1 | 2/1999 |

(Continued)

OTHER PUBLICATIONS http://www.conductiveinkjet.com/downloads.html; Conductive Inkjet Technology Limited Cambridge 08 PowerPoint Presentation.

(Continued)

*Primary Examiner* — Brian J Sines
(74) *Attorney, Agent, or Firm* — Roche Dignostics Operations, Inc.

(57) ABSTRACT

A biological test member, and method of making the same, is disclosed with the member including a substrate. The test member has usefulness, for example, in testing a person's blood glucose level. A first layer and a second layer of conductive metal are printed or otherwise applied on the substrate in an electrode pattern. The metal or metals are cured or sintered at a low, non-damaging temperature, such as by applying one or more pulses of a high-energy broad spectrum light. A layer of reagent may be provided on said second metal layer.

11 Claims, 9 Drawing Sheets

(56) References Cited

U.S. PATENT DOCUMENTS

| | | |
|---|---|---|
| 7,285,198 B2 | 10/2007 | Douglas |
| 7,368,331 B2 | 5/2008 | Hirai |
| 7,387,903 B2 | 6/2008 | Sakai et al. |
| 7,393,081 B2 | 7/2008 | Maekawa et al. |
| 7,501,289 B2 | 3/2009 | Kubo et al. |
| 2003/0081463 A1 | 5/2003 | Bocian et al. |
| 2005/0103624 A1 | 5/2005 | Bhullar et al. |
| 2005/0130397 A1 | 6/2005 | Bentley et al. |
| 2005/0153078 A1 | 7/2005 | Bentley et al. |
| 2005/0196322 A1 | 9/2005 | Truex et al. |
| 2006/0291772 A1 | 12/2006 | Haiml et al. |
| 2007/0048789 A1 | 3/2007 | Truex et al. |
| 2007/0207548 A1 | 9/2007 | Blankenstein |
| 2008/0152792 A1 | 6/2008 | Lian et al. |
| 2009/0208734 A1 | 8/2009 | Macfie et al. |

FOREIGN PATENT DOCUMENTS

| | | | |
|---|---|---|---|
| WO | WO 99/60169 A1 | 11/1999 |
| WO | WO 03/038886 A1 | 5/2003 |
| WO | WO 2004/011672 A1 | 2/2004 |
| WO | WO 2005/056875 A2 | 6/2005 |
| WO | WO 2005/106445 A1 | 11/2005 |
| WO | WO 2006/020507 A1 | 2/2006 |
| WO | WO 2006/037527 A1 | 4/2006 |
| WO | 2006/071419 A3 | 7/2006 |
| WO | WO 2008/012512 A2 | 1/2008 |
| WO | 2009/056299 A1 | 5/2009 |

OTHER PUBLICATIONS http://www.conductiveinkjet.com/downloads.html; Conductive Inkjet Technology Limited presentation, "Breakthrough inkjet technology for direct write of conductive metals onto non porous materials", 2006.

http://www.novacentrix.com/images/downloads/PF_Brochure_4pg.pdf, Novacentrix PulseForge Overview, "Advanced Curing for Printed Electronics—Cure Inks and Films at Room Temperature in Less than a Millisecond", Jul. 2008.

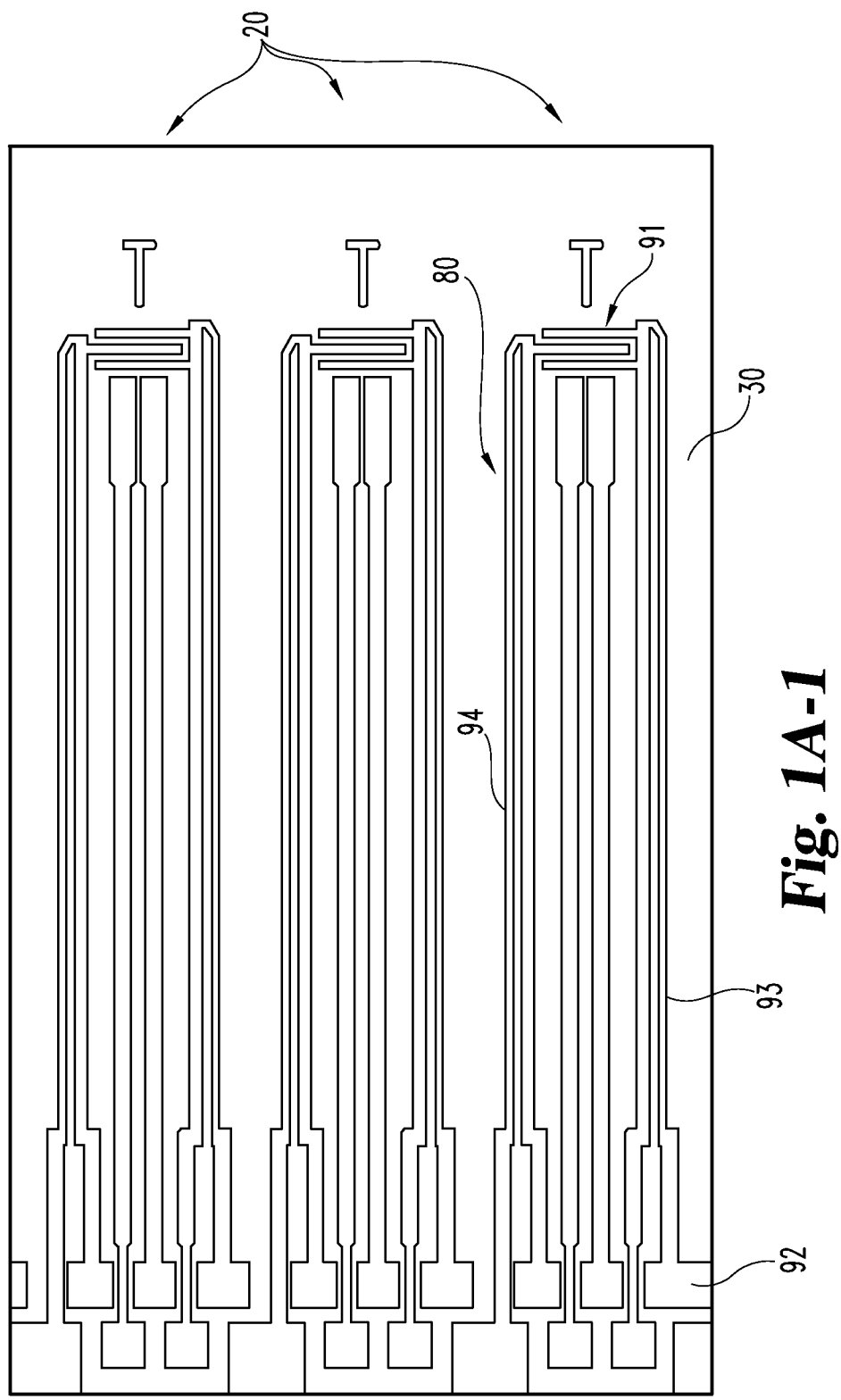

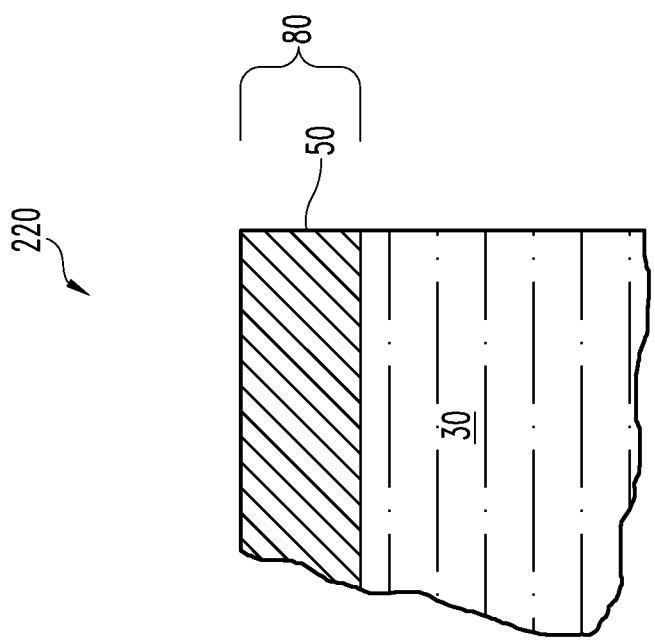

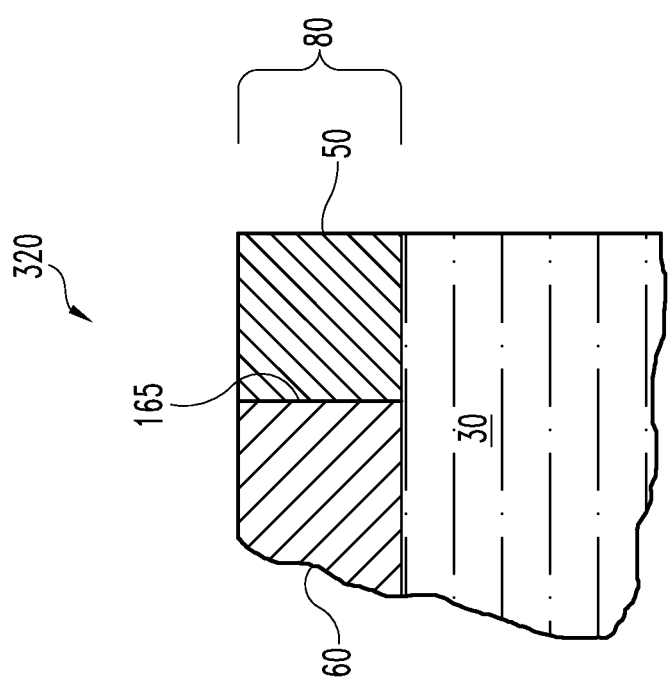

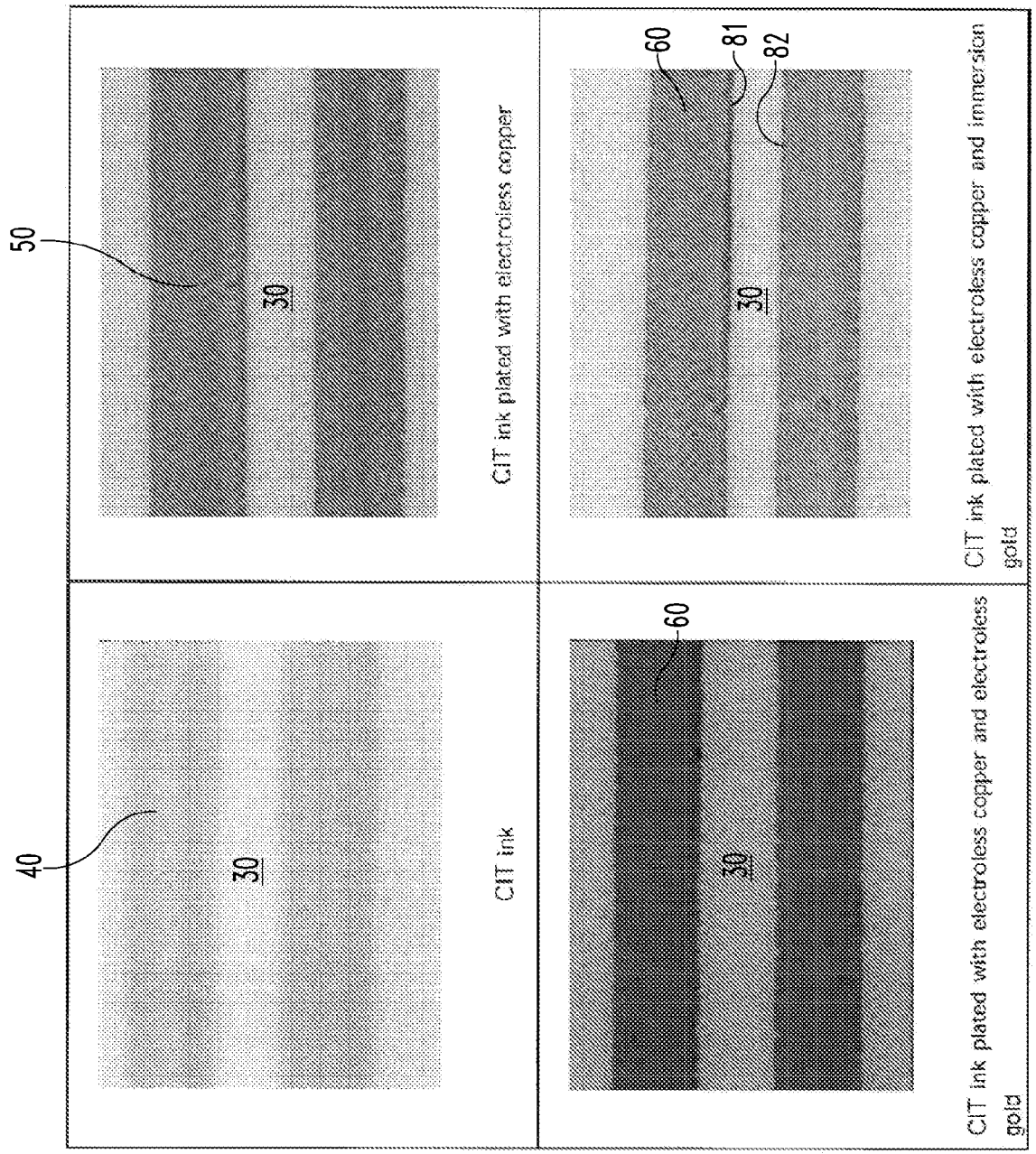
Fig. 2 CIT ink
Fig. 3 CIT ink plated with electroless copper
Fig. 4 CIT ink plated with electroless copper and electroless gold
Fig. 5 CIT ink plated with electroless copper and immersion gold

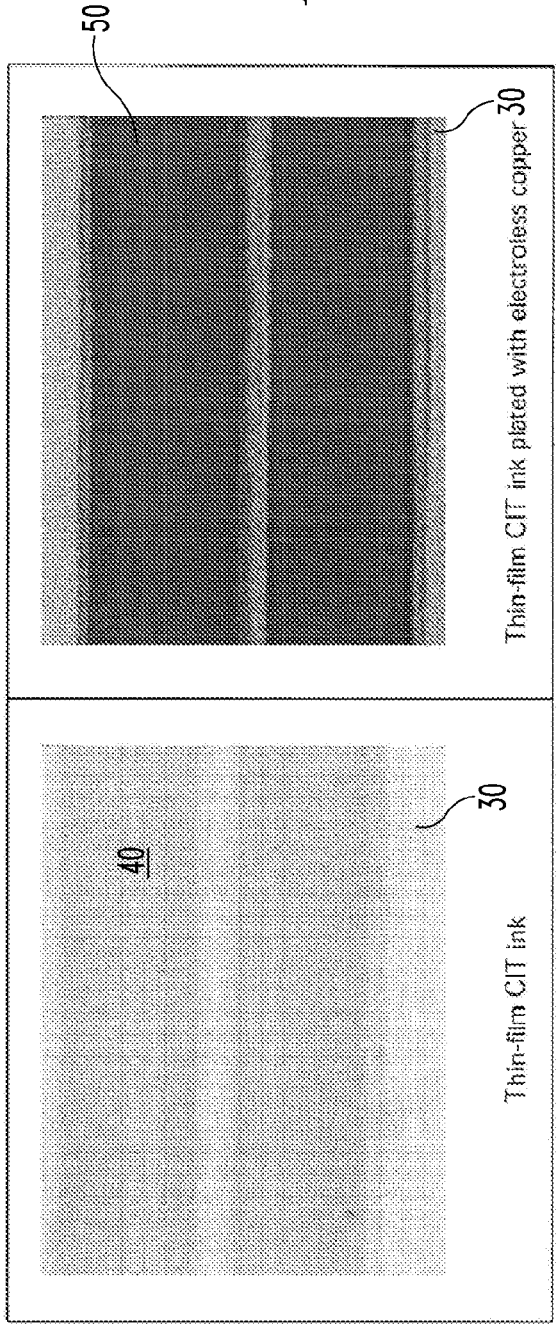
Fig. 6
Fig. 7
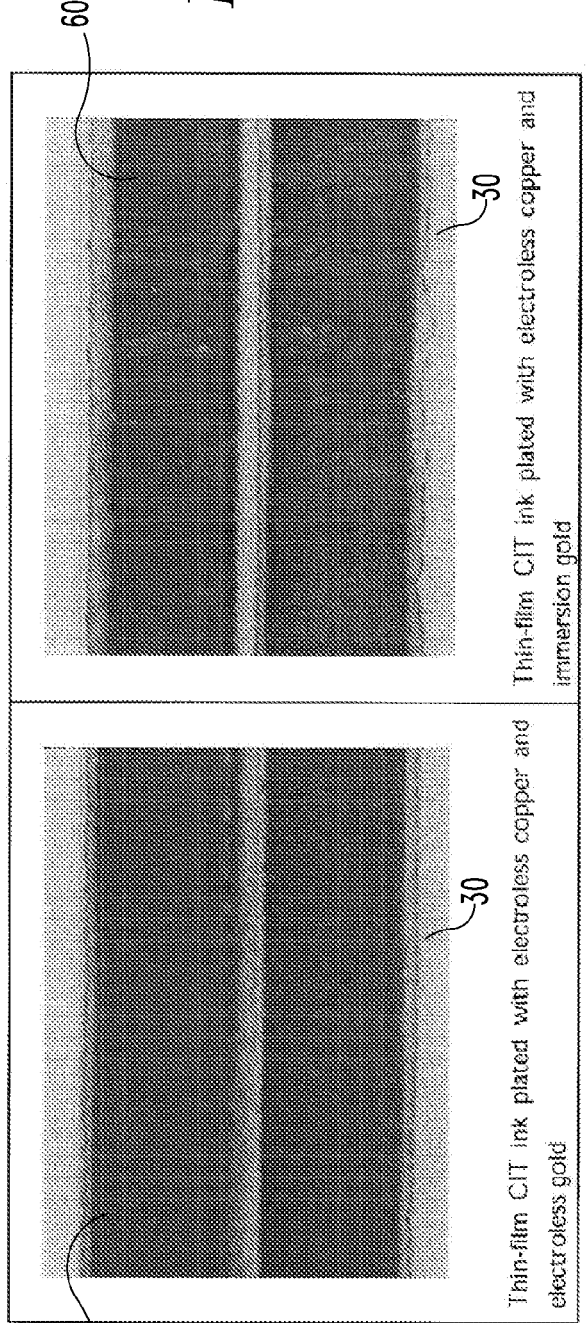
Fig. 8
Fig. 9

BIOSENSOR TEST MEMBER AND METHOD FOR MAKING THE SAME

This application is a divisional of application Ser. No. 12/862,262, filed Aug. 24, 2010, which is hereby incorporated by reference, and priority is claimed thereon.

FIELD OF INVENTION

The present invention is in the field of biosensor testing members, such as for example, test strips. These have usefulness, for example, in testing a person's blood glucose level.

BACKGROUND

The present invention is an improvement on prior test strips and how they are made. The present test members have usefulness in a variety of indications, including but not limited to blood testing (such as for glucose levels), as well as for bG testing, ketone testing, HbA1c strips, coag testing, continuous monitoring, and otherwise.

Currently, in some strips metal tracks are produced by sputtering a very thin layer of gold across the entire substrate reel and then using laser ablation or laser scribing to pattern the tracks, laser ablation in particular enabling a higher degree of accuracy. This is a subtractive process which results in loss of precious metal (some of which can later be reclaimed) as well as significant energy usage.

Other methods involve additive steps, such as inkjet printing and otherwise, to the extent disclosed in U.S. Patent Publication Nos. 2005/0130397 and 2005/0153078 to Bentley et al., but fail to disclose other features and benefits set forth herein.

One object is to provide an improved test member and a method for making the same.

SUMMARY

This object and others that may be set forth herein or otherwise appreciated by those of ordinary skill in the art in view of this disclosure are achieved by the present invention. The present invention may include a biosensor test member which may include a substrate and a conductive layer of one or more metals, normally in an electrode pattern. These metals may be alone or combined, or in separate layers, abutting, and/or a combination thereof. They may be sintered together. One or more pulses of high-energy, broad spectrum light may be used to sinter the metals. In certain aspects of the present invention, exposure to such pulses for any purpose may be referred to as "pulse forging". The metals may be applied by printing, high speed or otherwise. They may be in an ink carrier and cured on the substrate.

Also, a layer of electrically conductive first metal may be provided on a layer of ink substantially coinciding with said electrode pattern. There may also be another layer of electrically conductive metal thereon. Typically, the second metal is different from the first metal. Normally, a layer of reagent is put on that metal layer, and in one embodiment that second metal is substantially non-reactive to the reagent.

Electrical traces having different electrical resistivity may be on the test strip, such as for machine readable calibration, lot identification or otherwise. Such resistivity may be controlled by using different amounts of curing, such as by one or more pulses of high-energy, broad spectrum light, for different traces or portions thereof.

The present invention may include methods of producing a test member.

BRIEF DESCRIPTION OF THE DRAWINGS

FIG. 1A-1 is a top plan view of one example of a device according to the present invention. FIG. 1A-1 shows three such devices grouped or ganged on a single substrate, for later separation.

FIG. 1A-2 is a bottom plan view of one example of a device according to the present invention. FIG. 1A-2 shows three such devices grouped or ganged on a single substrate, for later separation.

FIG. 1E is an alternative partial side cross-section through an electrical trace.

FIG. 1F is an alternative partial side cross-section through an electrical trace.

FIG. 2 is a photograph of conductive inkjet technology ("CIT") ink on a substrate.

FIG. 3 is a photograph of CIT ink plated with electroless copper on a substrate.

FIG. 4 is a photograph of CIT ink plated with electroless copper and electroless gold on a substrate.

FIG. 5. is a photograph of CIT ink plated with electroless copper and immersion gold on a substrate.

FIG. 6 is photograph of thin-film CIT ink on a substrate.

FIG. 7 is a photograph of thin-film CIT ink plated with electroless copper on a substrate.

FIG. 8 is a photograph of thin-film CIT ink plated with electroless copper and electroless gold on a substrate.

FIG. 9 is a photograph of thin-film CIT ink plated with electroless copper and immersion gold on a substrate.

BRIEF DESCRIPTION OF THE PREFERRED EMBODIMENTS

Figures 1, 1A, 2:
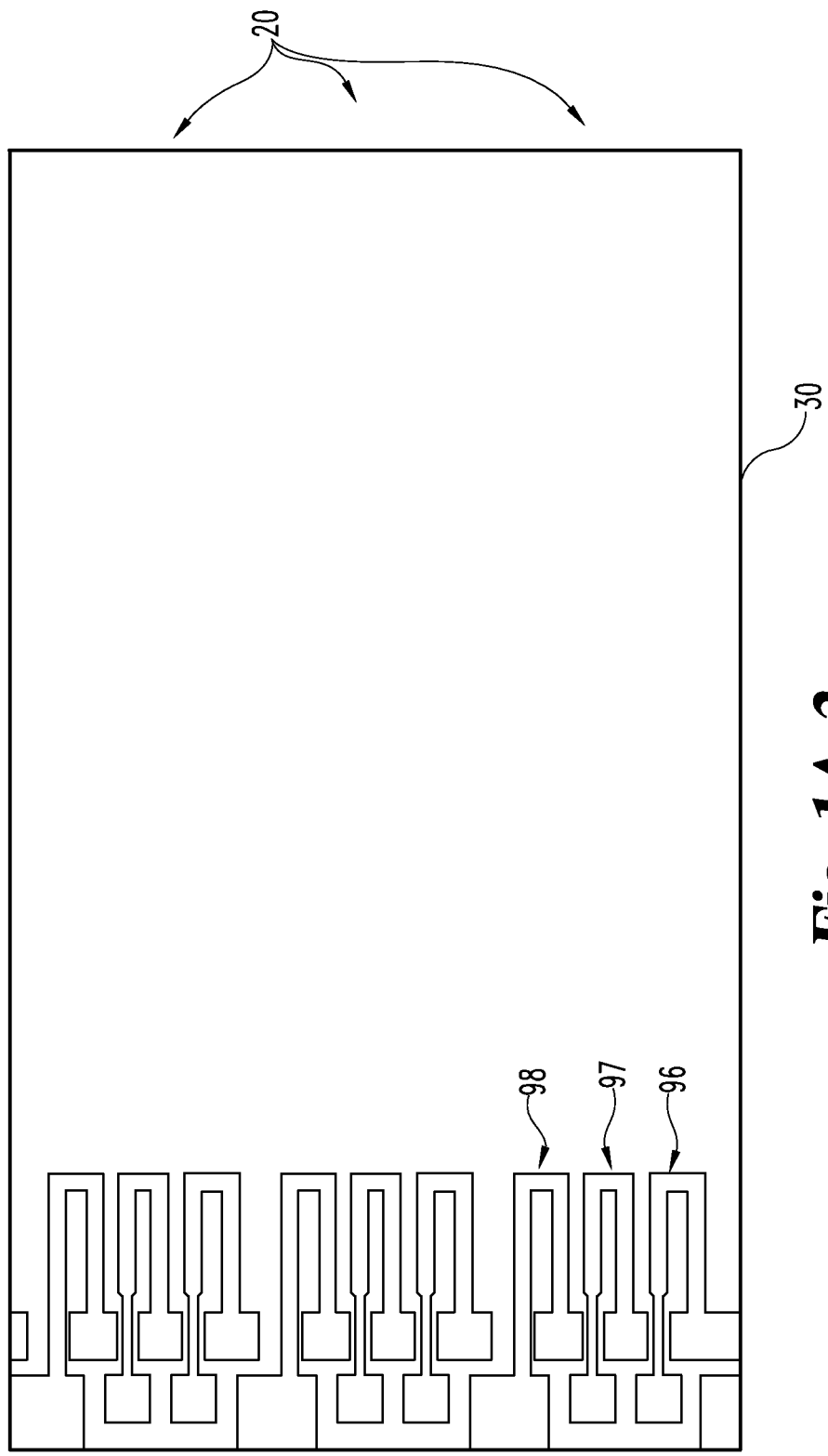

For the purposes of promoting an understanding of the principles of the invention, reference will now be made to the examples, sometimes referred to as embodiments, illustrated and/or described herein. Those are mere examples. It will nevertheless be understood that no limitation of the scope of the invention is thereby intended. Such alterations and further modifications in the described processes, systems or devices, any further applications of the principles of the invention as described herein, are contemplated as would normally occur to one skilled in the art to which the invention relates, now and/or in the future in light of this document.

As used in the claims and the specification, the following terms have the following definitions:

The term "cured ink" means ink in a solid or semi-solid form, having been dried, fused and/or solidified (by evaporation or otherwise), heated, exposed to chemical reaction, and/or exposed to high-energy pulsed light and/or some form of energy or radiation, such as ultraviolet (UV) light or otherwise, and/or any combination thereof.

The term "electroless plating" means depositing, plating or otherwise covering a receptive surface without the use of applied electrical current. This includes, but is not limited to immersion plating, such as for example, immersion plating of gold onto copper or onto nickel or onto both. Note that "electroless" herein is synonymous with the term, "electrodeless".

The term "electroless plating bath deposit" means a solid deposit, plating or other layer of electrically conductive metal from an electroless plating process.

The term "high-energy broad spectrum light" means light, (visible, invisible, or both) in the electromagnetic spectrum having: (a) an energy at or greater than about 180 joules, and optionally but more preferably greater than about 2000 joules; and, (b) having more than one wavelengths of light having a frequency variance of at least about 180 nanometers, and optionally but more preferably a frequency variance of at least 1100 nanometers apart. This may, but does not necessarily include pulse forging.

The term "high speed printing" means printing at a linear rate of a medium upon which that is being printed about 3 meters per minute or faster.

The term "inkjet printing" means a printing process in which droplets of ink issuing from nozzles are directed onto a surface, such as a substrate under computer control. This also encompasses jet printing, continuous jet printing or other printing with any kind of drop-dispense technology.

The term "laser ablated" means removal of a material, typically at or to define an edge, by irradiating it with a laser beam, and herein also includes laser scribing.

The term "low temperature photonic energy" means energy transferred by photons (including light as well as all other forms of electromagnetic radiation, including as a force carrier for electromagnetic force or energy) in an amount that maintains the average temperature of the matter it is acting upon below about 80 degree Celsius, and optionally, but more preferably below about 26 degrees Celcius. This may, but does not necessarily include high-energy broad spectrum light and/or pulse forging.

The term "polymer" means a long molecule made up of a chain of smaller, simpler molecules. This may include a product of polymerization. This may be natural, synthetic or both. This may include carbohydrates, such as cellulose, proteins and plastics. Polymer, as used herein, also includes materials which are combination and/or composite of polymers and non-polymers.

The term "precipitated solute" means a solid plating, layer or other deposit of a substance which had been previously dissolved or otherwise suspended in a solution or bath.

The term "printing" means the application of ink or ink-like material on a solid surface. This may include liquid inks, dry particle inks, and combinations thereof and otherwise. This may include offset printing, laser and otherwise. Printing may incur with pressure or non-pressure, contact or non-contact, and/or may include electro-static and/or non-electro-static application.

The term "pulse forging" means exposing to one or more pulses of a high-energy photonic energy. This may be a strobe pulse or otherwise. A "pulse" as used herein (such as with respect to pulse forging, low temperature photonic energy, and/or high-energy broad spectrum light, or otherwise), indicates that the light is normally applied only for short durations, typically between about 100 microseconds and 1 millisecond. Normally, such pulsed light or other energy is not applied continuously, but rather for these short pulse durations.

The term "reagent" is a substance for use in a chemical reaction to detect, measure, examine or produce other substances. In the context of the present device these are typically crystalline, powder or other solid form deposited on the device. For biological testing, typically they are for testing the concentration of analytes in the fluid (typically blood or other body fluid). Typically, this is for facilitating electron transfer between electrodes in such a fluid. Commonly they are or include a glucose enzyme. However, they may be or include other enzymes and/or non-enzymes and/or other fillers and/or chemicals.

The term "reference metallic electrical trace" means a trace that is used at least in part for having an electric current pass through it and the magnitude and/or other attributes of such an electrical current and/or electrical signal thereof are measured for comparison to some other value.

The term "RFID tag" means a radio frequency identification tag. This may be active, passive or both. This may be a stand alone, pre-manufactured tag and/or a printed circuit otherwise.

The term "sinter" means to cause to form a coherent mass, typically of one or more metals, by heating without melting, by pressure, or by other non-molten process and/or by a combination thereof.

The term "substrate damage temperature" means the temperature above which a substrate melts, burns, warps, or otherwise substantially deforms. This will vary from material to material. Such temperature may also be a function of time and temperature.

The language used in the claims is to only have its plain and ordinary meaning, except as may be explicitly defined herein. Such plain and ordinary meaning is inclusive of all consistent dictionary definitions from the most recently published general usage Webster's dictionaries and Random House dictionaries, and is inclusive of the meaning generally given to such language according to the general knowledge of a person of ordinary skill in the art.

Referring to the drawing figures, these are only examples of the invention, and the invention is not limited to what is shown in the drawings. For an example in the figures, and in particular FIG. 1A-1 through FIG. 1F, a biosensor test member 20 may comprises a substrate 30, and a layer 40 of cured ink in a printed electrode pattern 80 on said substrate. Layer 50 of an electrically conductive first metal is shown overlying the ink 40 and substantially coinciding with said electrode pattern 80. Layer 60 of an electrically conductive second metal is shown overlying layer 50, also substantially coinciding with the electrode pattern 80. Typically, the second metal (for example gold or gold alloy) is different from the first metal (for example copper or copper alloy). A layer of reagent 70 may be provided on and covering the metal layer 60 and/or on substrate 30, typically overlying at least in part electrode pattern 80. Normally, layer 70 covers substantially more than just pattern 80, at least at the reaction end 91. Optionally, however, layer 70 could be made to substantially coincide with pattern 80, or conversely to substantially not coincide with pattern 80, such as lying interstitially between edges 81 and 82 (see FIG. 1B). A variety of traces may be provided. For example traces 93 and 94 provide for a circuit with edges 81 and 82 lying in a mid-region of such circuit. Other shapes and arrangements may be used as well. For example, the two central traces illustrated may be used for confirming proper dosing.

Figure 1B:
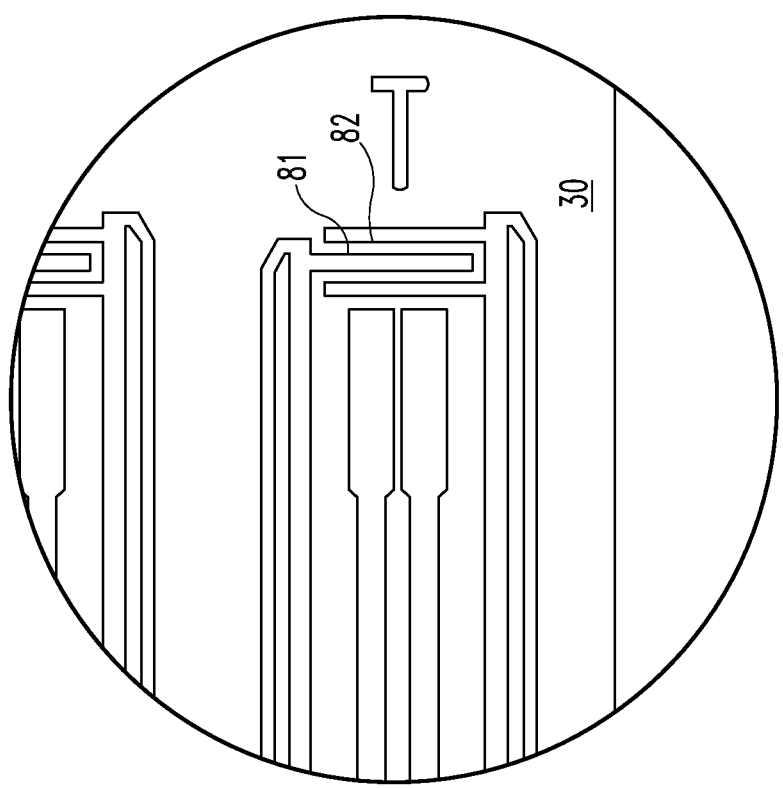
FIG. 1B is a top plan detail of the device of FIG. 1A.

With reference to FIG. 1A-2, an optional back side of test member 20 may be illustrated. Substrate 20 is as previously described. Also, as previously described, this illustrates three members together which later in the production process may be cut or otherwise separated. One, two, three or more reference metallic electrical traces may be present. For example, reference metallic electrical traces 96, 97 and 98 are illustrated as mere examples. These may be used for calibration, identification, lot coding, and/or a combination thereof, and/or otherwise. As illustrated, for example, metallic electrical trace 96 is generally "U" shaped, with contact pads at one end, and with the general length of the trace doubling back from one pad to the next. However, any arrangement may be used, including having such traces transverse to the width of the strip, curvilinear, serpentine, or otherwise. Additionally, reference metallic electrical traces need not necessarily be on the back side of a test strip. They may be on the front side, lateral side and/or a combination thereof as desired, depending on size and space constraints on the front and back surfaces of the substrate 30. Additionally, such reference metallic electrical traces may be present with dual or multiple functions. For example, the present invention optionally could be modified such that traces 93 and/or 94, or other traces illustrated in FIG. 1A-2, also function as reference metallic electrical traces, in addition to other functions.

Optionally, the attributes of such reference traces may be varied. For example, curing or other pulse forging or other treatment of respective electric traces 96, 97, 98 different from each other may be done to alter the resistivity of such traces. As such, for example, exposing a first reference metallic electrical trace 96 to more curing than a second reference metallic electrical trace 97 and/or 98, may result in a differential electrical resistivity as between the traces sufficient to allow machine reading of test strip attributes based on that differential. This may include lot coding, calibration, or otherwise. Also, optionally instead of or in addition to varying the time and/or intensity of curing, pulse forging, etc., a differential resistance and/or resistivity may be accomplished by exposing various lengths of various traces to such curing, pulse forging, etc. This likewise may vary among all three (96, 97 and 98) or more traces for more coding combinations.

Layer 70 generally comprises a reagent. In one embodiment, metal 60 comprises a material that is substantially non-reactive to reagent 70. Conversely, in other embodiments, reagent 70 is reactive (undesirably, such as corrosive or otherwise) with the first metal layer 50, and is thus generally located so that it does not contact first metal layer 50. In various embodiments, reagent 70 is configured for testing the concentration of an analyte in a liquid, such as a glucose enzyme or otherwise. Reagent 70 may be printed (such as by inkjet printing) or otherwise applied or coated. One approach is to apply the reagent by inkjetting with piezo electric ink jet heads, which optionally allows printing different reagent formulations over and/or adjacent one another. Hence, dual layers or more of reagents may be applied. It is also possible to apply reagents (for example Ag/AgCl chemistries) at or near a reference electrode to enhance test strip accuracy.

Optionally, one or more hydrophilic compounds may be on part or all of reaction end 91, substrate 30, or otherwise to facilitate fluid contact with reagent 70 and/or with electrodes, such as for example at or near edges 81 and 82. Such hydrophilic agent may be separate from and/or included as part of reagent 70.

Metal 50 and metal 60 may be kept as separate masses or may be sintered together. If sintered, they may be sintered essentially as a whole, but also may be sintered only primarily at their interface. Also, third and/or other layers, such as third metal layers (not drawn) may be included in the device, sintered or not. Sintering may be accomplished in any number of known sintering techniques.

Figure 1C:
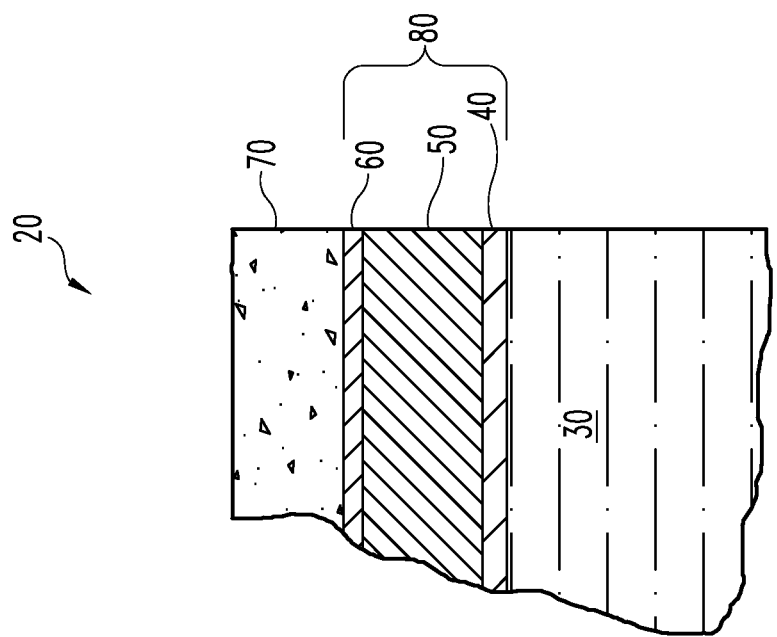
FIG. 1C is a partial side cross-section through an electrical trace of the device of FIG. 1A.
Figure 1D:
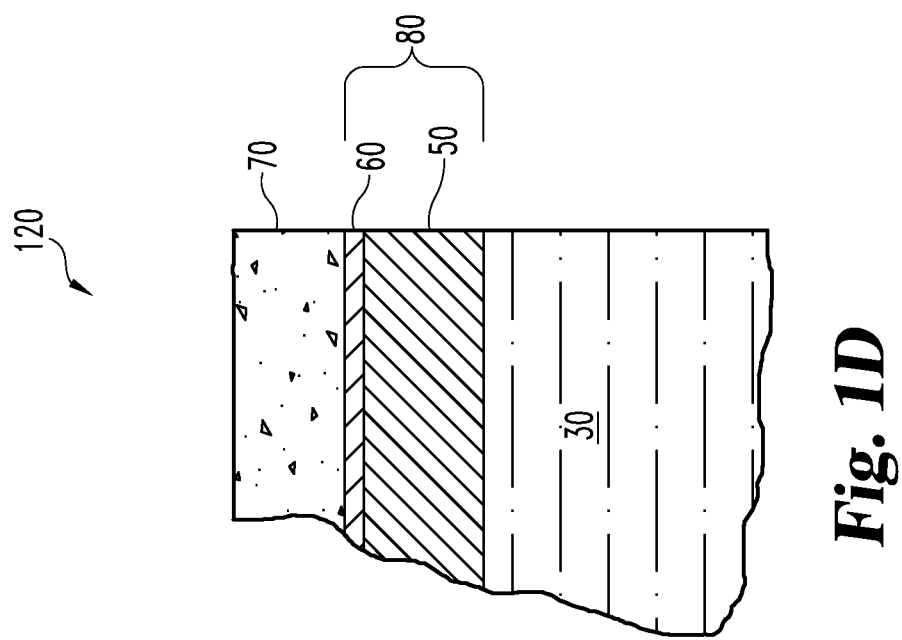
FIG. 1D is an alternative partial side cross-section through an electrical trace.

FIG. 1D shows an alternative test member 120. This is similar to test member 20 shown in FIG. 1C except that the layer of ink 40 has been optionally omitted. Metal 50 and metal 60 are provided. Reagent 70 is illustrated, but optionally may be omitted as well.

FIG. 1E illustrates test member 220, again another alternative. In this illustration pattern 80 comprises, and indeed may consist of, or consist essentially of, metal 50. As illustrated, member 220 does not have a reagent, though optionally it may have a reagent such as reagent 70 shown in FIG. 1D. Metal 50 may be a single metal, and/or may be an alloy, and/or it may be a blend or other combination of two or more metals. For example, metal 50 may be a combination of metal particles suspended in an ink binder or matrix. Such suspended particles may be subsequently sintered together. Optionally, they may be sintered by pulse forging or otherwise.

FIG. 1F shows another optional example of a test member 320. In this illustration, pattern 80 is shown as a first metal 50 and second metal 60. Note that in this example, such metals abut one another such as at abutment interface 165. As before, optionally, a reagent layer, such as reagent layer 70 (not shown in FIG. 1F) may be provided on top of the pattern 80, or not. It also may be provided over one metal, such as metal 50, but not the other metal, or partially over one or both. In addition to the two metals 50 and 60 abutting at interface 165, one or more additional layers (not shown) may overlay one or both metal portions 50 and 60, including spanning the abutment 165. As before, such metal layers may actually comprise particles or other suspended metal in an ink or carrier, and may be sintered together and/or may be sintered partially together at an interface. Similarly, with reference back to FIG. 1D, such partial sintering together in an interface may occur, as shown in FIG. 1D, at the interface between metal 50 and metal 60.

The arrangements of FIGS. 1B, 1C, 1D, 1E and/or 1F, as well as other arrangements and features as described, may be isolated, combined or mixed and matched with each other. Those are merely samples.

In embodiments in which an ink is used, it is desirable but not generally required to select an ink whose curing is accomplished without damage to substrate 30, such as may be caused by excessive time and/or temperature in heat curing the ink. The ink may be cured optionally by applying a high-energy strobe pulse of photonic energy to the substrate, before or after the addition of the metal layers 50 and/or 60. One example of an optional treatment includes curing by the PulseForge™ 3100 while maintaining the substrate temperature below 50° C. or to otherwise cryogenically treat the metal, normally after it has been formed into layers 50 and/or 60 on a substrate, and ideally for only short periods of time.

Conductive metal tracks, also referred to herein as electrode patterns 80 (see FIG. 1A-1, 1C) may be produced using inkjet technology via conductive inkjet technology (CIT) in which a catalytic ink 40 (see e.g. FIG. 1C (not to scale)) is typically printed, cured using UV radiation, and plated with a metal 50 (typically copper or nickel) and/or 60 (typically gold). In one embodiment, electroless plating processes are used. Through this method, conductivity approaching that of bulk metal can be achieved. Optionally, ink 40 may be printed using other techniques, including laser printing, contact printing, rotary screen printing, flexo printing, gravure or otherwise. For embodiments in which inkjet printing is used, high resolution deposition can be advantageous for optimal use of the resulting biosensor test member. In one embodiment, an inkjet printer is able to print down to 100 μm lines and spaces and smaller, such as inkjet printing at 600 to 1200 dpi or better. However, other resolutions, higher or lower as desired, may be used.

Moreover, as mentioned the conductive metal may reside in, rather than merely on, the ink or printing.

In other embodiments, an additive process may be used to apply an electro-conductive material (e.g. traces 80), such as a metal and/or metal containing matrix or carrier, to a biosensor test member and then, for example, pulse forge the material to sinter it together. The additive process then may result in reducing the amount of material required as compared to a subtraction process such as etching, laser ablation or otherwise. The additive approach, alone or in combination with subtractive processes, allow similar edge qualities as an ablation technique but with less waste of expensive raw materials, such as gold. This also allows the forming of other components on the test strip such as machine readable and/or non-evident coding components, such as a barcode or a "data matrix code" or "DMC". In one particular example, the pulse forging allows for different degrees of curing which in turn can allow for the creation of conductive strips (for example, traces 96, 97 and/or 98) having different resistivity and/or different resistances and therefore can be used as identifiers for machine readable and/or non-evident coding purposes. The additive nature also optionally allows a zebra-striping to occur in which (multiple) ends of copper are abutted against (multiple) ends of gold or silver (see e.g. FIG. 1F) forming a striping in series. Optionally, other additive techniques besides CIT can be used, such as directly inkjetting the gold or other conductive metal ink onto the substrate. In one embodiment, a dry manner of application of the ink is used, although other non-dry and/or hybrid approaches may be used. In one instance, a 5 nanometer thickness of gold has been deposited onto a substrate by inkjetting, although greater or lesser thicknesses may be used. A characteristic of pulse forging is that it can cure without heating an underlying substrate. This additive process also allows the forming of different metallization areas. Pulse forging further allows machine readable and/or non-evident coding optionally to be formed without harming any enzymes or other chemistry in a reagent. Pulse forging techniques, furthermore, may allow line speeds of 30 to 60 meters/minute, and inkjetting allows more heads and allows faster drying which in turn reduces the size of the manufacturing line. Other examples of using this technique allows for the formation of RFID tags on a strip.

In one embodiment, edges, such as at least edges like 81 and 82 (see e.g. FIGS. 1B and 5), are spaced from each other by a predetermined spacing and have suitable line acuity for biological testing (such as, for example human blood glucose level testing). Such acuity may be desired to allow for a reliable, measurable, and predictable current signal for testing, e.g., blood glucose levels. In one embodiment, such edge acuity is less than about 50 μm. In other embodiments, edge acuity is less than about 20 μm, and can be down to less than about 10 μm. In some of the tested examples, edge acuity ranged on average from about 4-6 μm. Also, the standard deviation of the edge acuity ratios is typically less than about 30 μm, and has been shown to be less than about 15 μm and as low as less than about 10 μm. Such testing examples are discussed further, below, regarding line acuity of the edges. Such edge acuity may be achieved with the present disclosure, notably without laser or other ablation. Nevertheless, laser ablation can provide better line or edge acuity (e.g. less than an average of one μm), and the present invention optionally may be used with laser ablation, or in partial combination with laser ablation. For example, one may use laser ablation to define the edges of the pattern of metal layer 50 (such as copper), while instead using electroless plating rather than laser ablation, to establish the edges or some or all of metal layer 60 (such as gold). Moreover, one could do this, or complete ablation of layers 40, 50 and 60, but only at selected or critical locations, such as for example, at edges at reaction end 91, such as edges 81 and 82. These options allow one to reduce waste and cost recovery (such as of gold) while enhancing line or edge acuity and while potentially reducing electrical resistance from end 91 to end 92.

Metal layer 60 may be reduced in thickness from prior art approaches of about 50 nanometers (nm) of gold, to optionally about 15 nm or less, particularly with electroless plating of layer 60. In one embodiment, this new method and device may provide a total metal thickness for a trace (layers 50 and 60 together) of about 50 to 300 nm, with about two percent (2%) thickness control along the trace.

Some non-limiting examples and testing of CIT ink and thin-film CIT ink are set forth below.

A. EXAMPLES 1-6

Example 1-3

Standard CIT ink was printed onto polyester substrate 30 using an Omnidot 760 GS8 printhead to produce catalytic templates of circuits for biosensor test members. The original image used as the basis for the printed circuits is shown in FIG. 1A to form conductive metal circuits, or electrode pattern, used in the present biological test member, e.g. a biosensor. These templates were tack-cured during the printing process using a low-power UV source (Omnicure S2000. Exfo) in order to control dot gain and then fully cured using a Fusion Lighthammer 6 UV-curring tunnel. This formed Example 1 as shown in FIG. 2.

Thereafter, a first metal layer 50, namely in this case a layer of copper, was added, as shown in FIG. 3. This was done with the template being immersed into an Enplate 872 copper plating bath for 2 min at 45° C. to deposit copper. This completed Example 1 and the by-product is shown in FIG. 3.

Examples 2 and 3, shown in FIGS. 4 and 5 respectively, had gold added to the device of Example 1, per above.

Example 2—Electroless gold on electroless copper: As stated, the templates were first immersed into an Enplate 872 copper plating bath for 2 min at 45° C. to deposit copper, after which they were immersed into a borohydride-based electroless gold plating bath for 1-4 minutes. Gold was successfully plated over the copper tracks. See FIG. 4.

Example 3—Immersion gold on electroless copper: As stated, the templates were first immersed into an Enplate 872 copper plating bath for 2 minutes at 45° C. Gold was successfully plated over the copper tracks. See FIG. 5.

Example 4-6

Those Examples 1-3 (depicted in FIGS. 2-5) using CIT ink were then reproduced as Examples 4-6, but for the starting point, Example 4, using thin-film CIT ink substituted for the CIT ink of Example 1. Thus, Examples 5 and 6 otherwise are like and correspond to Examples 2 and 3, respectively, above. Some of such thin-film ink examples are shown in FIGS. 6-7 (Example 4), FIG. 8 (Example 5) and FIG. 9 (Example 6).

This thin-film ink (see FIG. 6) was solvent-based with a resin binder matrix to provide adhesion to the substrate. As such, the solids loading is much lower than that of the Standard CIT ink, which allows much thinner films to be produced. As with the Standard CIT ink investigation (Examples 1-3), plating tests were performed: electroless gold on electroless copper (Example 5), and immersion gold on electroless copper (Example 6). This particular thin-film ink has a high solvent content and therefore wets out on the substrate surface very well. The flow of the ink was somewhat reduced by heating the substrate from the reverse side immediately after printing. However, a significant amount of spreading still occurs.

B. ADHESION TESTING

Testing of adhesion of the tracks formed in Examples 2-3 above (using standard CIT ink) to a polyester substrate was performed using the tape test and showed good adhesion with very little (<10%) of the tracks being removed from the substrate. The tracks are also flexible and sufficiently durable to withstand a fingernail scratch test.

In the same testing, tracks formed in Examples 5-6 above (using thin-film CIT ink) were flexible and durable enough to withstand a fingernail scratch test; however, the adhesion was not as strong as that of the tracks produced using the standard CIT ink with about 50% of the metal lifting off during the tape adhesion test.

C. LINE QUALITY

Line Width and Edge Acuity

Ink jet printed and subsequently plated lines are, in these examples, slightly wider than the laser ablated gold lines due to the wetting of the ink just before it is tack cured using the UV lamp attached to the print head mount. The electroless copper plating step does not appear to significantly affect the average line width. The same can also be said of electroless gold plating. On the other hand, the immersion gold process appears to result in a significant increase in the average width of the lines, potentially signifying that the second metal 60, such as gold, deposited through this method is normally of lower density.

FIGS. 6-9 contain example images of the thin-film catalytic ink, which have been plated with electroless copper, electroless gold and immersion gold. In each case, faint borders can be seen on the edges of the lines, which is due to the slightly increased thickness in these areas created during the drying process for this ink. The lines are also clearly much wider than those produced using the standard CIT ink (FIGS. 2-5), as the solvent base of the formulation promotes increased substrate wetting.

The line width and raggedness of a specific section of the printed and plated circuits were analyzed using the ImageXpert™ image quality analysis system. The change in these values, as the printed catalytic ink sections were plated with copper and then further with gold, was tracked during this investigation. The specific sections chosen for this analysis were the two parallel electrodes at the center of the circuit template. See center of FIG. 1A. The edges of the lines show good edge acuity, though they exhibit greater raggedness when compared to those lines produced by laser ablation.

Tables 1 and 2, below, depict an example of the ImageXpert™ sequence used to generate the data shown further below in Tables 3, 5 and 6, pertaining to the CIT ink Examples 1-3.

TABLE 1

Device Report: Line Intercolour Bleed SQ 28/8/56 1:22

| Stat | Measurement Name | Value | Nominal | Minimum | Maximum |
|---|---|---|---|---|---|
| <F> | Left: Top edge Raggedness | 2.999 | 30.000 | 10.000 | 30.000 |
| <F> | Left: Bottom Edge Raggedness | 2.558 | 30.000 | 10.000 | 30.000 |
| <F> | Left: Width | 460.353 | 50.00 | 25.000 | 75.000 |
| <F> | Right: Top Edge Raggedness | 2.443 | 0.000 | 0.000 | 0.000 |
| <F> | Right: Bottom Edge Raggedness | 3.132 | 0.000 | 0.000 | 0.000 |

TABLE 1-continued

Device Report: Line Intercolour Bleed SQ 28/8/56 1:22

| Stat | Measurement Name | Value | Nominal | Minimum | Maximum |
|---|---|---|---|---|---|
| <F> | Right: Width | 449.590 | 50.000 | 25.000 | 75.000 |
| <F> | Ratio | 1.024 | 0.000 | 0.000 | 0.000 |

TABLE 2

Statistics Report: Line Intercolour Bleed SQ 68 Devices Inspected, 50 Pass (73.5294%)

| Measurement Name | Mean | Std. Dev. | Minimum | Maximum |
|---|---|---|---|---|
| Left: Top edge Raggedness | 8.5233 | 7.8691 | 0.0000 | 35.5747 |
| Left: Bottom Edge Raggedness | 16.7440 | 30.7109 | 0.0008 | 151.7476 |
| Left: Width | 583.7745 | 1009.2000 | 0.0219 | 4999.2430 |
| Right: Top Edge Raggedness | 10.2303 | 8.8318 | 0.0002 | 39.3994 |
| Right: Bottom Edge Raggedness | 13.8239 | 24.0036 | 0.0002 | 114.0403 |
| Right: Width | 508.9540 | 881.6408 | 0.0189 | 4199.7020 |
| Ratio | 1.0458 | 0.1050 | 0.9014 | 1.4521 |

Line Width:

Tables 3 and 4 contain the line width measurements of the samples printed with CIT ink (or thin-film CIT ink) and then plated with electroless copper and further with electroless or immersion gold. The width of the corresponding lines in a gold circuit from a prior art laser ablation production method is noted for comparison. Table 3 is for the CIT ink samples (Examples 1-3), whereas Table 4 is for the thin-film CIT ink samples (Examples 4-6).

TABLE 3

ImageXpert ™ line width measurements of CIT ink-based samples

| | Line Width/µm | | | |
|---|---|---|---|---|
| | Line (1) | | Line (2) | |
| Sample | Average | Standard Deviation | Average | Standard Deviation |
| Gold circuit template | 507 | 0.2 | 507 | 0.2 |
| CIT Ink | 514 | 40.6 | 530 | 58.8 |
| CIT ink plated with electroless copper | 509 | 41.7 | 496 | 56.5 |
| CIT ink plated with copper and electroless gold | 512 | 35.7 | 483 | 73.2 |
| CIT ink plated with copper and immersion gold | 573 | 58.6 | 571 | 35.9 |

TABLE 4

ImageXpert ™ line width measurements of thin-film CIT ink-based samples

| | Line Width/μm | | | |
|---|---|---|---|---|
| | Line (1) | | Line (2) | |
| Sample | Average | Standard Deviation | Average | Standard Deviation |
| Gold circuit template | 507 | 0.2 | 507 | 0.2 |
| Thin-film ink plated with electroless copper | 757 | 79.7 | 746 | 84.0 |
| Thin-film ink plated with copper and electroless gold | 666 | 81.7 | 697 | 70.3 |
| Thin-film ink plated with copper and immersion gold | 760 | 58.1 | 659 | 126.2 |

Edge Acuity:

The raggedness measurements of the two center electrodes in each sample are collected in Tables 5-8. Tables 5 and 6 are for the CIT ink samples (Examples 1-3), whereas Tables 7 and 8 are for the thin-film CIT ink samples (Examples 4-6). Once again, the measurements for a prior art laser ablated gold circuit are included for comparison. The edge raggedness of the printed and plated strips is greater than the laser ablated circuits.

TABLE 5

ImageXpert ™ line (1) raggedness measurements of CIT ink-based samples

| | Raggedness of Line (1)/μm | | | |
|---|---|---|---|---|
| | Top of Line | | Bottom of Line | |
| Sample | Average | Standard Deviation | Average | Standard Deviation |
| Gold circuit template | 0.784 | 0.020 | 0.761 | 0.020 |
| CIT Ink | 5.099 | 1.849 | 5.293 | 1.689 |
| CIT ink plated with electroless copper | 5.167 | 3.881 | 5.571 | 4.493 |
| CIT ink plated with copper and electroless gold | 3.641 | 0.304 | 4.014 | 1.302 |
| CIT ink plated with copper and immersion gold | 6.379 | 2.147 | 5.360 | 1.590 |

TABLE 6

ImageXpert ™ line (2) raggedness measurements of CIT ink-based samples

| | Raggedness of Line (2)/μm | | | |
|---|---|---|---|---|
| | Top of Line | | Bottom of Line | |
| Sample | Average | Standard Deviation | Average | Standard Deviation |
| Gold circuit template | 0.970 | 0.020 | 0.996 | 0.020 |
| CIT Ink | 8.1000 | 6.414 | 6.118 | 1.912 |
| CIT ink plated with electroless copper | 5.837 | 3.137 | 5.177 | 2.299 |
| CIT ink plated with copper and electroless gold | 4.319 | 2.361 | 4.343 | 1.063 |
| CIT ink plated with copper and immersion gold | 6.182 | 1.277 | 4.502 | 1.264 |

Regarding the thin-film CIT ink Examples 4-6, the greater wetting of this ink compared to standard CIT ink is also reflected in the raggedness values shown in Tables 7 and 8, below.

TABLE 7

ImageXpert ™ line (1) raggedness measurements of thin-film CIT ink samples

| | Raggedness of Line (1)/μm | | | |
|---|---|---|---|---|
| | Top of Line | | Bottom of Line | |
| Sample | Average | Standard Deviation | Average | Standard Deviation |
| Gold circuit template | 0.784 | 0.020 | 0.761 | 0.020 |
| Thin-film ink plated with electroless copper | 9.554 | 8.380 | 10.811 | 7.210 |
| Thin-film ink plated with copper and electroless gold | 14.257 | 11.299 | 8.175 | 6.067 |
| Thin-film ink plated with copper and immersion gold | 4.313 | 1.963 | 7.877 | 6.895 |

TABLE 8

ImageXpert ™ line (2) raggedness measurements of thin-film catalytic ink samples

| | Raggedness of Line (2)/μm | | | |
|---|---|---|---|---|
| | Top of Line | | Bottom of Line | |
| Sample | Average | Standard Deviation | Average | Standard Deviation |
| Gold circuit template | 0.970 | 0.020 | 0.996 | 0.020 |
| Thin-film ink plated with electroless copper | 10.016 | 6.377 | 9.324 | 7.372 |
| Thin-film ink plated with copper and electroless gold | 10.107 | 4.036 | 12.763 | 8.569 |

TABLE 8-continued

ImageXpert ™ line (2) raggedness measurements of thin-film catalytic ink samples

| | Raggedness of Line (2)/μm | | | |
|---|---|---|---|---|
| | Top of Line | | Bottom of Line | |
| Sample | Average | Standard Deviation | Average | Standard Deviation |
| Thin-film ink plated with copper and immersion gold | 6.609 | 4.282 | 7.903 | 4.227 |

D. ELECTRICAL RESISTANCE

The resistance of the copper and gold plated samples was measured across the length of one electrode. Such length is exemplified as running from reaction end 91 to contact end 92 (see FIG. 1A). The results are shown in Tables 9 and 10, below. The resistance of the prior art laser ablated gold circuits across this area is much greater than that for the printed and plated samples. Additionally, the presence of the gold plated on the top of the copper does not appear to affect the resistance of the strip, regardless of the method used for its deposition, i.e., immersion or electroless plating.

TABLE 9

Conductivity of CIT ink-based copper and gold-plated samples

| Sample | Average Resistance (O) |
|---|---|
| Gold circuit template | 89.3 |
| CIT ink plated with electroless copper | 3.2 |
| CIT ink plated with electroless copper and electroless gold | 3.2 |
| CIT ink plated with electroless copper and immersion gold | 3.1 |

Also, for the thin-filmed CIT ink, (FIGS. 6-9), the resistance of the top electrode was measured for each copper plated sample. This was then repeated after plating with gold and the average resistance values are shown in Table 10. It can be seen that the resistance and therefore conductivity of the printed and copper-plated samples of thin-layer CIT ink are the same or similar regardless of whether they are plated using an immersion or electroless gold plating process. This was also observed with the standard CIT ink copper-plated samples, in Table 9 above.

TABLE 10

Conductivity of thin-film CIT ink-based copper and gold plated samples

| Sample | Average Resistance (O) |
|---|---|
| Gold circuit template | 89.3 |
| Thin-film catalytic ink plated with electroless copper | 2.4 |
| Thin-film catalytic plated with electroless copper and electroless gold | 2.8 |
| Thin-film catalytic plated with electroless copper and immersion gold | 2.7 |

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A biosensor test member, comprising:
   an electrically conductive first layer comprising a first metal in an electrode pattern on a substrate such that said first layer has at least two electrode layer portions that are spaced from each other on said substrate; and
   an electrically conductive second layer comprising a second metal and located on and substantially coinciding with said electrically conductive first layer such that said electrically conductive second layer has at least two second layer electrodes portions that are spaced from each other on said substrate,
   wherein said second metal is different from said first metal, and said first metal and said second metal being at least partially sintered together, and wherein said first metal and said second metal each are in a cured ink carrier of the respective first layer and second layer.

2. The test member of claim 1 wherein said first and second metals are at least partially sintered by exposing them to a low temperature photonic energy.

3. The test member of claim 2, wherein said low temperature photonic energy maintains the temperature of said substrate below a substrate damage temperature, and wherein said substrate is not temperature damaged.

4. The test member of claim 1, and further comprising:
   a first reference metallic electrical trace and a second reference metallic electrical trace on said substrate; and,
   wherein said first reference metallic electrical trace is more cured than said second reference metallic electrical trace, wherein a differential electrical resistivity exists between said traces sufficient to allow machine reading of test strip attributes based on said differential.

5. The test member of claim 1, wherein said electrode pattern comprises at least a pair of edges spaced from each other on said substrate, said edges each having an average edge acuity ratio of less than about 20/μm and a standard deviation of said ratio of less than about 15/μm.

6. The test member of claim 1, and further comprising a third layer of a reagent on said electrically conductive second layer, wherein said second metal is substantially non-reactive to said reagent.

7. The test member of claim 3, and further comprising a third layer of a reagent on said electrically conductive second layer, wherein said second metal is substantially non-reactive to said reagent.

8. The test member of claim 2, wherein said low temperature photonic energy maintains the temperature of said substrate below a substrate damage temperature wherein said substrate is not temperature damaged.

9. The test member of claim 8, wherein said first metal and said second metal each are carried in a cured ink carrier of the respective first layer and second layer.

10. The test member of claim 9, wherein said electrode pattern comprises at least a pair of edges spaced from each other on said substrate, said edges each having an average edge acuity ratio of less than about 20/μm and a standard deviation of said ratio of less than about 15/μm.

11. The test member of claim 10, and further comprising a third layer of a reagent on said electrically conductive second layer, wherein said second metal is substantially non-reactive to said reagent.

* * * * *